United States Patent
Leighton

(10) Patent No.: US 6,468,783 B1
(45) Date of Patent: Oct. 22, 2002

(54) PUNCH-CHANGING TISSUE ARRAY INSTRUMENT

(75) Inventor: Stephen B. Leighton, Silver Spring, MD (US)

(73) Assignee: Beecher Instruments, Silver Spring, MD (US)

( * ) Notice: Subject to any disclaimer, the term of this patent is extended or adjusted under 35 U.S.C. 154(b) by 0 days.

(21) Appl. No.: 09/828,829

(22) Filed: Apr. 9, 2001

(51) Int. Cl.[7] .................................................. C12M 1/36
(52) U.S. Cl. ............................. 435/286.3; 435/284.1; 435/286.2; 435/307.1; 435/307.9; 422/63
(58) Field of Search ............... 422/63, 68.1; 435/286.2, 435/286.3, 284.1, 307.1, 309.1

(56) References Cited

U.S. PATENT DOCUMENTS 4,684,613 A * 8/1987 Barrere et al. ........... 435/286.3
4,979,093 A * 12/1990 Laine et al. .................. 700/61
6,103,518 A * 8/2000 Leighton ...................... 422/63
6,383,801 B1 * 5/2002 Leighton ...................... 422/63

* cited by examiner

*Primary Examiner*—David A. Redding
(74) *Attorney, Agent, or Firm*—Pendorf & Cutliff

(57) ABSTRACT

Arrays of biological tissue can be created by removing cores from regions of interest in a series of donor blocks of embedded tissues. The cores removed are placed in a regular array in a recipient block. This is typically done with two different punches, one for obtaining the cores of interest and the other for creating the receiving holes in the recipient block. The present invention comprises such a system including a single z axis, with a mechanism for automatically changing two or more punches in and out of a holder on the z axis.

14 Claims, 2 Drawing Sheets

PUNCH-CHANGING TISSUE ARRAY INSTRUMENT

BACKGROUND OF THE INVENTION

1. Field of the Invention

Arrays of biological tissue can be created by removing cores from regions of interest in a series of donor blocks of embedded tissues. The cores removed are placed in a regular array in a recipient block. This is typically done with two different punches, one for obtaining the cores of interest and the other for creating the receiving holes in the recipient block. The present invention concerns a simplified and economical system and device for creating tissue arrays.

2. Description of the Related Art

Biological tissue arrays consist of regular arrays of cores of embedded biological tissue arranged in a sectionable block typically made of the same embedding material (e.g., paraffin) used originally for the tissue in the cores. The new blocks may be sectioned by traditional means (microtomes etc.) to create multiple nearly identical sections each containing dozens, hundreds or even over a thousand different tissue types. These sections may be used for histochemical and other assays. Any test performed on any one of these sections is effectively performed on hundreds of samples at once. The result is a tremendous saving in effort and time and some increase in the availability and precision of control samples.

Tissue arrays have been constructed entirely manually (Battifora, H., "The multitumor (sausage) tissue block: novel method for immunohistochemical antibody testing", Laboratory Investigation Vol. 55, pp. 244–248, 1986) and with the assistance of mechanical mechanisms (Kononen et al., "Tissue microarrrays for high-throughput molecular profiling of tumor specimens", Nature Medicine Vol. 4, Number 7, pp. 844–847, July 1998) for a variety of biological applications. A manual instrument has also been described in Leighton, U.S. Pat. No. 6,103,518 "Instrument for constructing tissue arrays". Semiautomatic systems have also been proposed (Leighton U.S. patent application Ser. No. 09/811,963 entitled "Double Z-Drive Tissue Array Instrument", incorporated herein by reference). The manual methods have largely been superceded by those aided by instruments due to the speed, precision and increased density of the latter. In these devices, two hollow needle-like punches are used, one slightly smaller (recipient punch) than the other (donor punch) to create a hole in a recipient block, typically of paraffin or other embedding medium. The larger or donor punch is used to obtain a core sample from a donor block of embedded biological tissue of interest.

The punches are sized such that the sample obtained just fits in the hole created in the recipient block. Thus the sample is a snug fit in the recipient block and a precise array can be created.

The recipient block is held in an appropriate fixture during the entire process—although it may be removed and alternatingly replaced with one or more other recipient blocks to create more than one array from one set of donor blocks. Micrometer drives or other precision linear positioning means position the punches with respect to the recipient block or the recipient block with respect to the punches. It is clearly desirable that the donor punch reach exactly the same position that the recipient punch reaches on the recipient block for a given setting of the micrometer drives. If it does not, the retrieved sample will not pass smoothly into the hole just created for it, but instead will be damaged or lost. It is further desirable that this motion be created reliably and inexpensively.

In Kononen et al it is taught to use slides and drive mechanisms to first move the recipient punch into a central position and, alternately, the donor punch. This mechanism is cumbersome, expensive, slow and prone to misalignment errors. The use of slides at an intermediate angle such as 45 degrees, as taught by Kononen et al is particularly problematic, as small errors in height positioning can lead to corresponding errors in lateral position and vice versa.

Leighton U.S. Pat. No. 6,103,518 entitled "Instrument for constructing tissue arrays") teaches a turret or other means allowing two punches to share a single z axis slide or drive. This mechanism is appropriate for a simple, manually operated instrument, but may be awkward for an automated instrument in which all motions are driven by powered actuators (pneumatic, electric etc.). Special mechanisms must be machined and assembled, and standard components are not available.

While the above systems are operable, there remains a need for a system which can be fully automated yet has fewer robotic parts than the above-described systems.

SUMMARY OF THE INVENTION

It is the purpose of the present invention to allow a standard laboratory robot to be adapted to make tissue arrays. In addition, it is the purpose of the present invention to provide a means for constructing a robust automated instrument.

After extensive investigation, the present inventor realized that in all of the prior art it has been the conventional thinking that the two different punches should be held permanently in some part of the mechanism or drives. Apparently, it may have been thought that permanently holding the punches in respective holders was necessary in order to guarantee accuracy and correct alignment, or that primary goals of operational simplicity and speed in a single, dedicated machine blinded those working in this art to the possibility of using a single set of x-y-z axes and then adding a mechanism for alternately placing first one and then the others of two or more punches into position on the working end of one of the axes.

The present inventor has now surprisingly discovered that the duplex robotics of the prior art are not required, and has developed a simple and precise means of forming tissue arrays by alternately positioning the two different punches in any tissue array instrument.

The invention comprises completely separating the two punches (donor and recipient), giving each their own stylet (unlike Kononen et al) and using a single z-drive (unlike the double z drive disclosed in the Leighton patent application) but not resorting to a cumbersome turret or slider means (as disclosed e.g. in Leighton U.S. Pat. No. 6,103,518 "Instrument for constructing tissue arrays"). The improvements over the prior art include using changeable punches that can automatically and alternately be held by a moving gripper and actuator.

The x, y and z drives that are present for general positioning in most laboratory robots can be simply programmed not only to bring the active punch to the appropriate position with respect to a donor or recipient block and to do the punching, but also to bring the punch holder to a magazine or storage area, to release one punch, and to acquire another.

The positions of the tips of the two punches can be periodically measured automatically by sensors mounted on the same pallet as the donor and recipient blocks. Whenever their positions may have moved (perhaps due to encountering a more dense block or irregularity, or perhaps by being disturbed by an operator or foreign object, or simply being altered by virtue of a new punch being installed) then the new positions can be measured and the measurement automatically used to update the offset value. Sensing the tip positions with a sensor mounted on the block holding pallet allows a system to be constructed with standard components and to be robust in the face of environmental challenges and mechanical drift. The position sensing may be used to overcome any variation in tip position caused by alternately replacing the punches automatically.

Typically, the punches are stored in simple holders attached to the same substrate that holds the donor and recipient blocks and a complementary holder or gripping means is attached to a member or arm that can move in x, y and z with respect to said substrate. (Of course, there are various combinations of motion that are obvious to one skilled in the art, such as having the substrate fixed with respect to the laboratory frame of reference and the arm moving in x, y and z or the substrate moving in x an y and the arm moving only in z or the substrate moving in x and the arm moving in y and z etc. The reference to movement in the z axis should be understood as relative movement between punch and donor or recipient block.) The holder or gripping means can be switched between a gripping and releasing mode by the same computer or controller that is controlling the rest of the operations of the instrument, or the gripping and releasing may be entirely mechanical, activated by the approach and withdrawal motions of the gripper with respect to the holding location.

Once the appropriate punch is firmly held in the gripping means, the motion drive can move the punch to the appropriate position for punching holes in a recipient block, discharging waste to a waste receptacle, acquiring tissue from a donor block, or inserting tissue into a recipient block. A surface sensing device could either be permanently attached to the moving arm or could be an alternate tool that can be picked up when needed instead of one of the punches.

Since each of the two punches can be picked up and used by the same axis, only one x, y, z drive system is required. Compare Kononen et al, where six drives are required, two for moving the two punches into and out of position, one for moving the punches into and out of the blocks and two for x, y motions of the blocks. In Leighton (U.S. Pat. No. 6,103,518 "Instrument for constructing tissue arrays"), manual operation is contemplated, but were the system to be automated, four drives would be required, and they would need to be of two different types, one for toggling the turret from one position to the other, and another for moving the turret up and down. This would result in greater costs, as two different types of drives would be required to be designed and manufactured for the two different types of motion.

In the present invention, a standard laboratory robot can be used, leading to reduced costs and simplicity.

While two punches are employed in the above discussion for simplicity, it will be readily understood that it is easily within the scope of this invention to use more than two punches, each stored in a similar holder on the substrate, for example to permit quick changes between different sizes of punches for different applications. It is also possible to use the punch holder to hold a tool for moving blocks, a tool for labeling blocks, or other tools or devices.

The rest of the system may be similar to that already described in the prior art. For example, powered or manual micrometer drives or the like may be used to position the punching mechanism over the blocks or the blocks under the punching mechanism. A removable bridge may be used for supporting the donor blocks over the recipient blocks, or the donor blocks may be attached to the same pallet that holds the recipient blocks. The latter arrangement allows the same x and y drives and slides to be used for both donor and recipient blocks. Alternately, separate x, y systems could be used for the recipient blocks and the donor blocks. This is more complicated, but can permit faster operation for high-throughput systems.

The foregoing has outlined rather broadly the more pertinent and important features of the present invention in order that the detailed description of the invention that follows may be better understood, and so that the present contribution to the art can be more fully appreciated. Additional features of the invention will be described hereinafter, which form the subject of the claims of the invention. It should be appreciated by those skilled in the art that the conception and the specific embodiments disclosed may be readily utilized as a basis for modifying or designing other tissue arrayers for carrying out the same purposes of the present invention. It should also be realized by those skilled in the art that such equivalent structures do not depart from the spirit and scope of the invention as set forth in the appended claims.

BRIEF DESCRIPTION OF THE DRAWINGS

For a fuller understanding of the nature and objects of the present invention reference should be made to the following detailed description taken in conjunction.with the accompanying drawings in which.

DETAILED DESCRIPTION OF THE INVENTION

The invention will now be described in greater detail by reference to the drawings.

Figure 1:
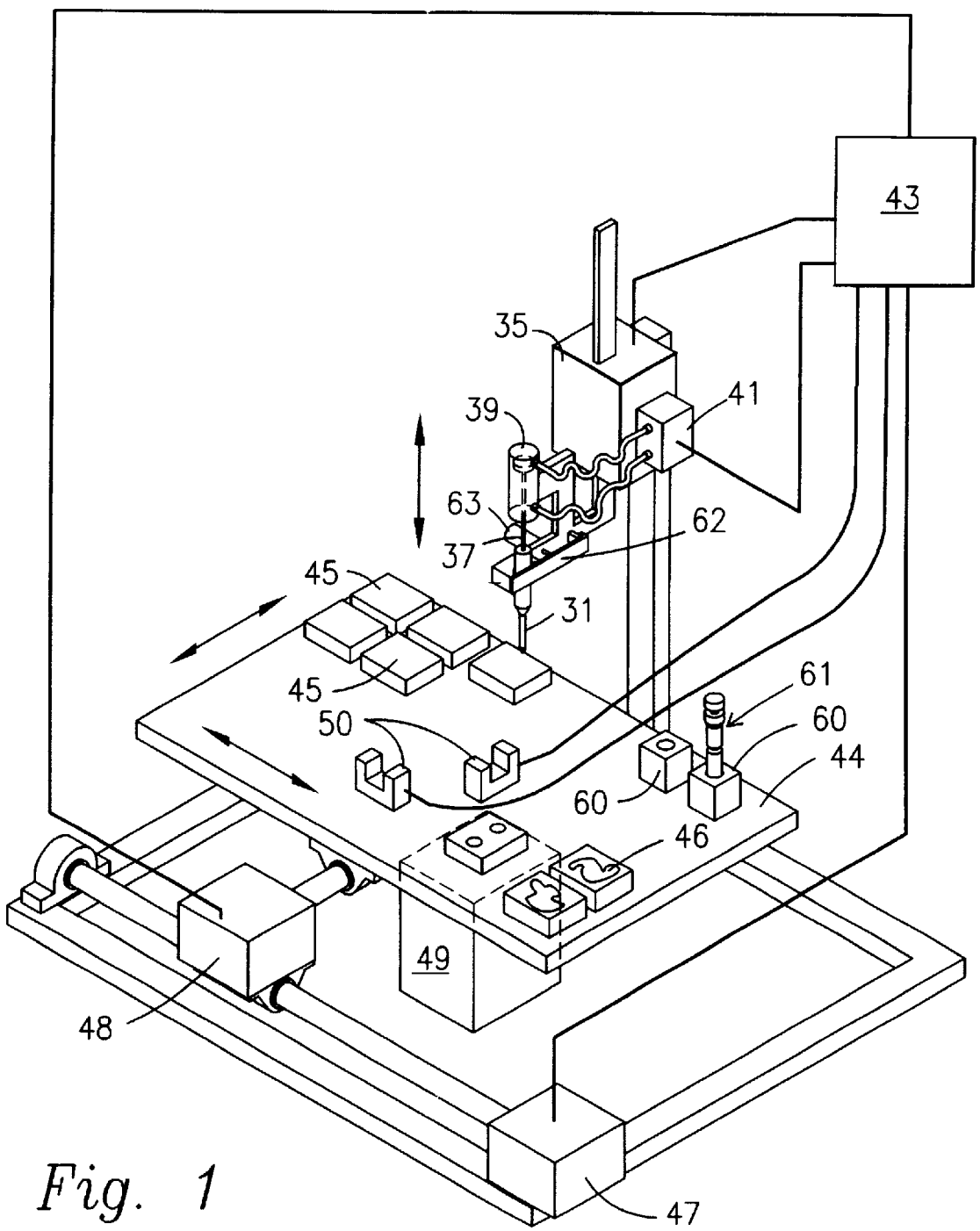
FIG. 1 is an isometric semi-schematic drawing of the punch-changing tissue array instrument.

In FIG. 1 there is illustrated a punch-changing tissue array instrument wherein punch 31 is held by arm 33 and moved vertically by drive 35. Coaxially inside the punch is stylet 37 moved by drive 41 for the stylet actuator and moved vertically relative to the punches by actuator 39. A computer 43 controls all of the drives or actuators. A pallet 44 is moved in the x and y directions by actuators 47 and 48. The pallet holds recipient blocks 45, donor blocks 46, a waste receptacle 49 and a sensor 50. The sensor allows the computer to find the position of the punches with respect to the pallet. Other sensors, limit switches, encoders and feedback elements may be employed but are not shown for clarity of the illustration, and since their use is well know in the art.

Figure 2:
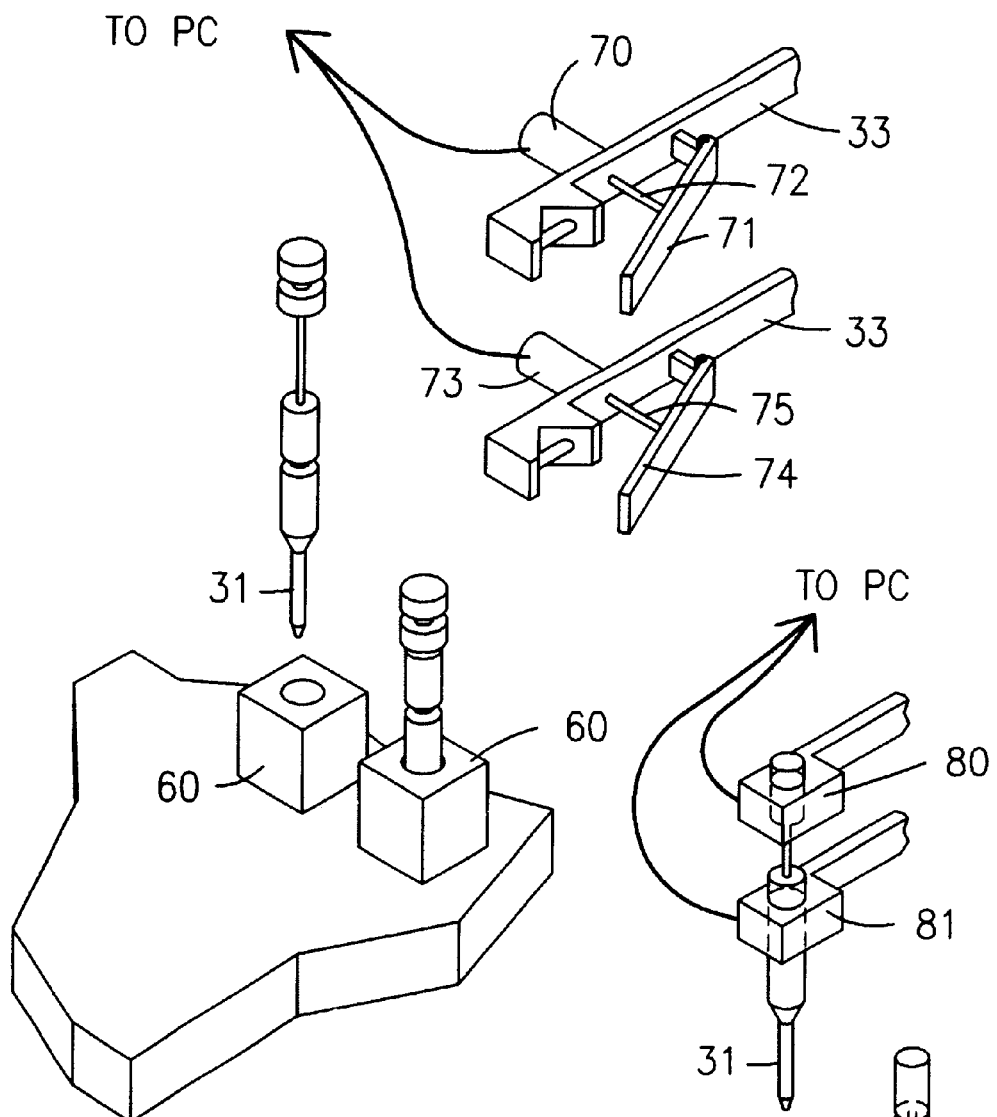
FIG. 2 is a detailed view of a clamp-type gripping mechanism.

FIG. 2 shows a dual clamping mechanism as one possible type of gripping mechanism. Computer controlled solenoids 70, 73 are connected to clamping jaws 71, 74 via actuating arms 72, 75. The upper clamping jaw grips the stylet hub and is connected to the stylet drive, the lower clamping jaw grips the punch hub and is connected to the punch drive.

Figure 3:
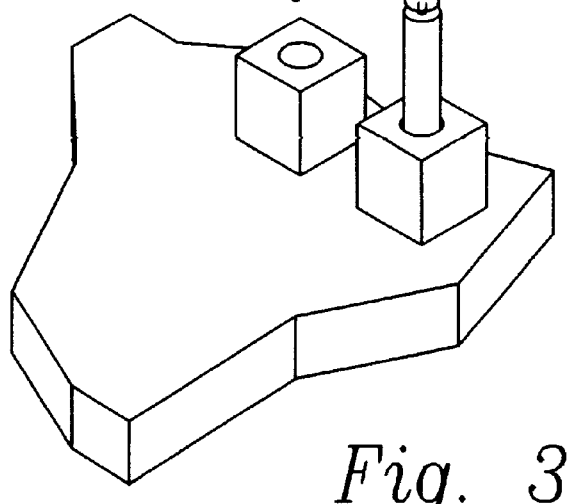
FIG. 3 is a detailed view of an orifice-type gripping mechanism.

FIG. 3 shows an alternative dual gripping mechanism. Stylet gripper 80 has an orifice slightly larger than the stylet hub. Punch gripper 81 has an orifice slightly larger than the punch hub. Upon activation of hydraulic (e.g., balloon seal, hydraulic clamping jaws), electromagnetic, or vacuum suction means, the stylet gripper and punch gripper grip the stylet and punch, respectively.

It is preferred that the gripper be provided with a register, which may be a simple "V" shape, against which the stylet or punch hub is positioned for precise positioning.

Obviously, the grippers can be designed and operated similarly, or the grippers can be of different type.

Although there are many ways to construct the punch-changing tissue array instrument, one preferred embodiment will now be described in greater detail. Two punches, a recipient and donor punch, are stored, each in a separate holder on a substrate which also holds the donor and recipient blocks (FIG. 1). Each is provided with a stylet for pushing wax or tissue out of the punch. Either punch/stylet assembly can be brought under the gripper of the z-axis (FIG. 2) with the same x, y traverse system that is used to move the donor and recipient blocks. The z axis is then used to move the gripper down and grasp the punch that is required for the next operation. When it is necessary to change to a different punch, the empty punch holder 60 is brought under the gripper of the z-axis drive and the z axis drive lowers and releases the punch that is no longer required. The z axis drive then lifts the empty gripper, the other punch is brought underneath the gripper, and the z-axis drive lowers the gripper to acquire the target punch.

As a punch is acquired, its stylet is connected to the stylet drive in the same operation. The stylet of the active punch may be driven by a simple pneumatic cylinder. The pneumatic cylinder allows precise positioning of the stylet in either the fully up or fully down position, and also allows controlled forces at intermediate positions for tamping the cores, merely by adjusting the air pressure. It would also be within the scope of the invention to use an electromechanical actuator (with force sensor if necessary) instead of the pneumatic cylinder, or to use pneumatic or hydraulic cylinders for positioning the punch.

Preferably, electromechanically driven slides position a pallet in the x and y axes to allow precise positioning of a set of one or more recipient and donor blocks under the punch. All of the motions may be under electronic and computer control by any of many well know means—e.g., limit switches, sensors, position feedback, stepper and/or servo motors and the like.

A typical cycle consists of the desired recipient position being brought under the recipient punch by the x-y drives; the recipient punch being moved by its z drive to penetrate and remove a blank core, creating a pocket for later use; the recipient punch being brought (by the x-y drives) near a waste receptacle (which may be mounted on the same x-y pallet as the blocks) and the recipient stylet being moved to discharge the blank core into the waste receptacle; the recipient punch being returned to its holoder and the donor punch acquired, the desired position of a donor block being brought by the x-y drives under the donor punch; the donor punch being moved by its z drive to penetrate and remove a desired core of tissue; the previously created pocket in one of the recipient blocks being brought by the x-y drives under the donor punch; and finally the donor punch being brought in contact or nearly in contact with the recipient block by its z drive and then its stylet being moved to implant the tissue core in the pocket created in the recipient block. Next, the lateral position is incremented with drives X and or Y to the next position and the cycle is repeated.

It is within the scope of the patent that either the blocks or the punches can be moved in x, y and z directions relative to the laboratory frame of reference—only relative motion matters in this invention.

Wadding or Packing at the End of the Stylets

Wadding or packing may be provided at the end of the stylets to seal the gap between the stylet and the punch to keep the core from being extruded along the stylet and damaged and/or lost.

In the prior art, the stylets are metal wires sliding in the metal punch tubes. This rather crude arrangement is functional but, depending on the tissue type, temperature and closeness of fit of the wire and the tube, some of the tissue can extrude between the wire and the tube, leading to unpredictable losses of tissue. In addition to the simple loss of the tissue, this causes the additional problem of a different volume of tissue beneath the stylet and arrays being constructed with non-uniform depths. This non-uniformity leads to a much reduced yield of useful sections that can be cut from the array block.

The present invention comprises the use of small pieces of wadding or packing at the tips of the stylets to prevent this extraneous extrusion. These pieces can preferably be elastomeric material such as polyurethane, natural rubber or polyvinyl chloride or the like. They can be made to fit the punches exactly by using the punch as a tool to punch exactly the correct size disc from a sheet of the chosen material.

Force Control of the Stylet

A drive for the stylet can be designed to exert prescribed forces as well as moving to precise positions, to allow tamping of the cores for better grip by the punches and easier removal of the cores from the blocks.

The closest system of which the inventor is aware for automated tissue arrayers uses only positional control of the stylet. This has the disadvantage that the stylet can only be withdrawn entirely out of the way of the tissue or wax cores while they are being acquired or pushed down flush to the end of the punch to insert the tissue core in a recipient block. Although intermediate positions are possible in theory, they are not useful as the automated machine has no information on the exact length of the wax plug with which to calculate an appropriate intermediate position for the stylet. There are combinations of tissue type, wax type, temperature and punch geometry for which it has been a problem to reliably extract the core from the block. Although the punch may have cut out a core, it is not removed because it is still held at the bottom by the block and there is not enough friction along the sides of the punch to grip the core and break the connection to the block at the bottom.

The present invention includes controlling the force applied to the stylet such as by means of a pneumatic or hydraulic cylinder. This controlled force can be set high enough to push the core completely out of a punch into a tissue block or at an intermediate value for tamping the core just before it is withdrawn. The tamping compresses the core axially and thus expands it radially against the cylindrical walls of the punch. This increased radial force creates a stronger grip of the punch on the core and enables the punch to extract the core. This phenomenon is somewhat counterintuitive as some users of earlier automated machines thought that the axial force would push the core completely out of the punch. Indeed it would push it out if large forces were used to force the stylet all the way to the end of the punch tube. Earlier descriptions of automated machines teach simple cycles involving the stylet either being at one end of its full stroke or the other.

The controlled force may be exerted by any number of ways well known in the art, such as pneumatics, hydraulics, controlled current motors, feedback systems involving force sensors on any sort of actuator or combinations of springs and various mechanisms.

It can be seen that there are many combinations and permutations possible with advantages for different applications. The key element that all have in common is the use of at least two separate z drives.

Further, in order to increase the range or capacity of the unattended instrument, it is possible to further provide a magazine containing donor and/or recipient blocks, either fresh or punched, wherein the magazine is operatively associated with said instrument for providing blocks to said instrument and/or receiving blocks from said instrument.

Although this invention has been described in its preferred form with a certain degree of particularity with respect to an instrument for creating micro-arrays with punches moveable on z axis, it is understood that the present disclosure of the preferred form has been made only by way of example and that numerous changes in the details of structures and the composition of the combination may be resorted (e.g., donor and recipient block holding pallet moving in z direction) to without departing from the spirit and scope of the invention.

Now that the invention has been described,

I claim:

1. An instrument for constructing arrays of tissue in a recipient block, the instrument comprising:
    first and second punch units, each punch unit comprising a punch including a punch hub and a stylet including a stylet hub,
    means for holding at least one donor block,
    means for holding at least one recipient block,
    gripper means for releasably precisely holding one of said punches at a time,
    means associated with said gripper for moving said stylet hub relative to said punch hub,
    means for precisely moving and positioning said punch hub relative to at least one of said donor and recipient block holders,
    wherein said gripper means is adapted for receiving, moving, and releasing said punches individually.

2. An instrument as in claim 1, wherein said gripper is provided with means for movement in the z axis.

3. An instrument as in claim 1, wherein said donor and recipient block holders are provided with means for movement in the x and y axes for selectively repositioning said recipient block holder and said donor block holder relative to said gripper.

4. An instrument as in claim 1, wherein said donor block and recipient block holders are provided on a turntable rotatable about a z axis.

5. An instrument as in claim 1, wherein one or more of the motions are under computer or manual control via powered drives.

6. An instrument as in claim 1, wherein the donor block holder and the recipient block holder are provided on different platforms.

7. The instrument as in claim 6, wherein one of said the donor block holding platform and recipient block holding platform is moveable in at least one of an x and y axis, and wherein the other of said platforms is formed by a turntable rotatable about the z axis.

8. The instrument as in claim 1, wherein the donor block holder and the recipient block holder are provided on the same platform.

9. An instrument as in claim 1, further comprising an amount of compliant wadding material provided inside the punch at the tip of the stylet.

10. An instrument as in claim 1, wherein said compliant wadding material is an elastomer.

11. An instrument as in claim 1, wherein said stylets are driven by an actuator. which can exert controlled forces.

12. An instrument as in claim 1, wherein the stroke length of said stylets can be controlled via said stylet actuators.

13. An instrument as in claim 12, wherein the stylet actuators are controlled for stroke length via a computer.

14. An instrument as in claim 1, further comprising a magazine containing blocks, and operatively associated with means for providing blocks to said instrument and/or receiving blocks from said instrument.

* * * * *